United States Patent [19]

Kiyoura

[11] Patent Number: 5,608,114
[45] Date of Patent: Mar. 4, 1997

[54] DISPROPORTIONATING METHOD OF TRIMETHYLAMINE

[75] Inventor: Tadamitsu Kiyoura, Kawasaki, Japan

[73] Assignee: Mitsui Toatsu Chemicals, Inc., Tokyo, Japan

[21] Appl. No.: 356,642

[22] Filed: Dec. 15, 1994

[30] Foreign Application Priority Data

Dec. 28, 1993 [JP] Japan ................................. 5-335501
Mar. 16, 1994 [JP] Japan ................................. 6-045543

[51] Int. Cl.$^6$ .............................................. C07C 209/64
[52] U.S. Cl. ................................... 564/499; 564/470
[58] Field of Search ........................... 564/470, 474, 564/499

[56] References Cited

U.S. PATENT DOCUMENTS

| | | | |
|---|---|---|---|
| 4,398,041 | 8/1983 | Cochran et al. | 564/479 |
| 4,485,261 | 11/1984 | Ashina et al. | 564/479 |
| 4,806,689 | 2/1989 | Gier et al. | 564/474 |
| 5,243,078 | 9/1993 | Agrawal | 564/470 |
| 5,344,989 | 9/1994 | Corbin et al. | 564/479 |

FOREIGN PATENT DOCUMENTS 57-169445 10/1982 Japan .
62-47172 10/1987 Japan .

OTHER PUBLICATIONS

Applied Catalysis, vol. 32, 1987, pp. 361–366, M. Keane et al, "Selective Synthesis of Dimethylamine Over Small Pore Zeolites".

Patent Abstracts of Japan, vol. 7, No. 135 (C–170), Jun. 11, 1983 (JP-A-58049340 (Toyo Soda Kogyo KK) Mar. 23, 1983.) *Abstract*.

*Primary Examiner*—Brian M. Burn
*Attorney, Agent, or Firm*—Burns, Doane, Swecker & Mathis

[57] ABSTRACT

Upon subjecting trimethylamine with ammonia and optionally, a methylamine to a disproportioning reaction to reduce the proportion of the trimethylamine, use of a zeolite as a catalyst, said zeolite being mordenite, clinoptilolite or the like at least 80% of whose ion-exchangeable cations being in the form of hydrogen ions, makes it possible to efficiently conduct the reaction at a low reaction temperatures and also to suppress by-production of impurities such as acetonitrile.

20 Claims, No Drawings

DISPROPORTIONATING METHOD OF TRIMETHYLAMINE

BACKGROUND OF THE INVENTION (i) Field of the Invention

This invention relates to a method for reducing the proportion of trimethylamine by a disproportionating reaction, said trimethylamine being by-produced in a small amount upon preparation of dimethylamine and monomethylamine through a reaction between methanol and ammonia in the presence of a shape-selective catalyst. More specifically, this invention pertains to a catalyst useful in allowing the disproportionating reaction to proceed efficiently and also in suppressing by-production of trace components which are formed in the disproportionating reaction.

(ii) Description of the Related Art

As catalysts for the disproportionation of trimethylamine, those having solid acidity are known to show catalytic ability for many years. As those exhibiting solid acidity, alumina, silica-alumina, silica-magnesia, alumina-titania, silica-titania, silica-zirconia, alumina-zirconia, solid phosphoric acid, large pore zeolites and the like are known to be effective for the disproportionating reaction. Among these solid acid catalysts, proposed and widely employed are those composed primarily of silica and/or alumina, specifically, silica-alumina catalysts (Japanese Patent Laid-Open No. 169445/1982, Japanese Patent Publication No. 47172/1987, U.S. Pat. No. 4,485,261) and rhenium-ion-exchanged zeolite Y (REY zeolite), i.e., "SK-500" (trade name; product of Union Carbide Corporation, U.S.A.; U.S. Pat. No. 4,398, 041).

The above-described conventional catalysts proposed to date do not have sufficient catalytic activities. A reaction temperature of 375° C. or higher is needed to achieve sufficient conversion of trimethylamine especially with an amorphous silica-alumina catalyst. This disproportionating reaction is an equilibrium reaction. Although a somewhat higher temperature is advantageous for the conversion at equilibrium, it may be sufficient in balance if the conversion at equilibrium available at about 300° C. is obtained. There is a demand for a catalyst which exhibits sufficient activities in a temperature range of about 280°–380° C., because this disproportionating reaction is an endothermic reaction and therefore, heat of reaction should be supplied from the outside to the catalyst layer. The lower the reaction temperature, the more advantageous in both apparatus and energy for supplying heat of reaction. From such a viewpoint, the above-described REY zeolite has the advantage that it shows activities at a lower temperature than an amorphous silica-alumina catalyst. According to the results of a test conducted by the present inventors, however, REY zeolite has been found to involve the problem that reaction by-products—for example, acetonitrile, acetone, propionitrile and propyl-amine—are formed in trace amounts. These trace by-products accumulate in the course of separation and purification of the reaction products, and cause the problem that the efficiency of the separation is lowered.

SUMMARY OF THE INVENTION

An object of the present invention is to provide a disproportionating method of trimethylamine, which is free of the drawbacks described above. More specifically, the object is to provide a method which allows a disproportionating reaction of trimethylamine to efficiently proceed at a reaction temperature lower than that needed when amorphous solid acid catalysts used widely to date, typified by silica-alumina catalysts, are employed and is free from by-production of trace components such as acetonitrile, acetone, propionitrile and/or propylamine.

The present inventors have conducted extensive research with a view toward developing a disproportionating method of trimethylamine, which is free of the above-described problems. As a result, it has been found that use of a zeolite with its ion-exchangeable cations having been sufficiently exchanged by hydrogen ions as a catalyst for the disproportionating reaction of trimethylamine allows the disproportionating reaction to efficiently proceed at temperatures lower than those needed for conventional catalysts without by-production of acetonitrile, acetone, propionitrile, propylamine and/or the like in trace amounts, leading to the completion of the present invention.

The present invention therefore provides a method for disproportionating trimethylamine by subjecting the trimethylamine and ammonia or the trimethylamine, ammonia and a methylamine to a disproportionating reaction to reduce the proportion of the trimethylamine. The disproportionating reaction is conducted in the presence of at least one zeolite selected from the group consisting of mordenite, clinoptilolite, heulandite, canncrinite, ferrierite, gmelinite, stilbite, mazzite, offretite and ZSM-5 zeolite, at least 80% of whose ion-exchangeable cations are in the form of hydrogen ions.

DETAILED DESCRIPTION OF THE PREFERRED EMBODIMENTS

It has heretofore been considered that among zeolites, those having a pore diameter of approximately 5 to 7 Å—such as mordenite and clinoptilolite—other than faujasite (pore diameter: 7.4 Å) and the like can hardly induce a disproportionating reaction of trimethylamine within their pores and the disproportionating reaction primarily proceeds on their outer surfaces alone because the molecular size of trimethylamine is 6.1 Å(Japanese Patent Laid-Open No. 169445/1982 and U.S. Pat. No. 4,485,261). It is also known that outer surfaces of a zeolite account for 5–10% or so of its entire surfaces. It is disclosed that, when a catalyst having a smaller pore diameter such as mordenite is used, the time of contact between a reactant or reactants and the catalyst has to be prolonged sufficiently (Japanese Patent Laid-Open No. 169445/1982 and U.S. Pat. No. 4,485,261).

Further, it is disclosed that, since 5 A zeolite, macroporous H-chabazite-erionite and H-mordenite are shape-selective, they are suited for the reaction between methanol and ammonia but are not suited for the disproportionating reaction of trimethylamine; for the disproportionating reaction, $SiO_2$—$Al_2O_3$, H—Y and REY zeolites are suited (U.S. Pat. No. 4,398,041).

According to research conducted by the present inventors, it has been unexpectedly found that a zeolite having a small pore diameter like mordenite or clinoptilolite can sufficiently promote the disproportionating reaction of trimethylamine even at a temperature lower than those required for amorphous solid acid catalysts employed widely to date, such as silica-alumina catalysts, can set the time of contact between the reactant and the catalyst either equal to or shorter than those needed for the silica-alumina catalysts and, when exchangeable cations are sufficiently exchanged with hydrogen ions, can minimize trace by-products such as acetonitrile to substantially zero.

Namely, byproducts such as acetone, acetonitrile, propionitrile and propylamine are formed where exchangeable cations in a zeolite have been substituted by cations of an alkali metal, an alkaline earth metal or rhenium. A zeolite whose cations have been sufficiently exchanged with protons however do not practically form these impurities.

The zeolite or zeolites usable in the practice of the method of this invention are each either synthetic or natural. Described specifically, the followings are examples of zeolites usable in the method of the present invention and their compositions and maximum pore diameters.

| Kind | Composition | Maximum pore diameter (nm) |
|---|---|---|
| Mordenite | $Na_8(Al_8Si_{40}O_{96})24H_2O$ | $0.67 \times 0.70$ |
| Clinoptilolite | $Na_6(Al_6Si_{30}O_{72})24H_2O$ | $0.44 \times 0.72$ |
| Heulandite | $Ca_4(Al_8Si_{28}O_{72})24H_2O$ | $0.76 \times 0.30$ |
| Canncrinite | $Na_6(Al_6Si_6O_{24})CaCO_3 \cdot 24H_2O$ | 0.59 |
| Ferrierite | $Na_2Mg_2(Al_6Si_{30}O_{72})18H_2O$ | $0.54 \times 0.42$ |
| Gmelinite | $(Na_2Ca)_4(Al_8Si_{16}O_{48})24H_2O$ | 0.70 |
| Stilbite | $Na_4Ca_8(Al_{20}Si_{52}O_{144})56H_2O$ | $0.61 \times 0.49$ |
| Mazzite | $(Na_2K_2CaMg)_5(Al_{10}Si_{26}O_{72})28H_2O$ | 0.74 |
| Offretite | $(CaMg)_{1.5}K(Al_4Si_{14}O_{36})14H_2O$ | 0.67 |
| ZSM-5 | $Na_n(Al_nSi_{96-n}O_{192})16H_2O$ | $0.56 \times 0.53$ |

Each of these zeolites can be used at the silica/alumina ratio in the above-described composition without any modification. In the method of the present invention, it is also possible to use that obtained by increasing the silica/alumina ratio upon hydrothermal synthesis of any one of the above zeolites or a high-silica zeolite with a high silica/alumina ratio attained by increasing the silica/alumina ratio of any one of the above zeolites in accordance with a method such as an acid treatment or steam treatment.

The high-silica zeolite catalyst with an increased silica/alumina ratio features relatively less deposit of carbonaceous substances during a long-term operation than low-silica zeolites and can hence minimize the reduction in catalytic activities.

A zeolite inherently having a high silica/alumina ratio (hereinafter abbreviated as the "R ratio"), instead of an R ratio increased specifically by a troublesome procedure such as an acid treatment, also features less deposit of carbonaceous substances and a smaller reduction in catalytic activities even when employed in a log-term operation.

Among a group of zeolites usable in the present invention, those inherently having a high R ratio, for example, 10 or greater—mordenite (R ratio: 10), clinoptilolite (R ratio: 10), ZSM-5 (R ratio>20) and the like—are therefore particularly preferred catalysts.

Faujasite (corresponding to synthetic Y zeolite) has a pore diameter as large as 0.74 nm. Its initial catalytic activities are excellent. However, its R ratio is 4.6, carbonaceous substances deposit in a relatively large amount and, when employed in a long-term operation, faujasite gives results inferior in the deterioration of activities to mordenite.

In the method of the present invention, exchangeable cations in a zeolite to be employed as a catalyst are fully exchanged with hydrogen ions to minimize, to substantially zero, acetonitrile and the like which are by-produced upon the disproportionating reaction. The functional exchange attainment to a H-type zeolite is 80% or higher, preferably 90% or higher.

To exchange cations of a zeolite, which has been exchanged with an alkali metal, an alkaline earth metal or the like, with hydrogen ions, there are two methods, one featuring an exchange treatment in a gas phase and the other an exchange treatment in a liquid phase.

To conduct the treatment in a gas phase, the zeolite is treated with vapor of ammonium chloride at 250°–300° C. and is then heated to 400°–600° C. or is treated at 400° C. with ammonia gas and is then heated to 500°–600° C., whereby the zeolite is converted into a hydrogen ion form. To treat the zeolite in the liquid phase, the zeolite to be exchanged is immersed in an aqueous solution of an ammonium salt such as ammonium nitrate or ammonium chloride, so that the zeolite is subjected to ion exchange. The concentration of the aqueous solution of the ammonium salt is often adjusted in a range of 0.1 to 2N. The aqueous solution of the ammonium salt is used in an amount equivalent to the amount of the ammonium salt 2 to 10 times as much as the amount of cations contained in the zeolite and to be ion-exchanged. The temperature upon conducting the ion exchange can range from room temperature to the boiling point of the aqueous solution of the ammonium salt. The time required for the ion exchange is often in a range of 1–30 hours. The ion exchange in the liquid phase can be conducted by conducting the above procedures once or more, generally, twice to thrice, whereby more than 90% of the ion-exchangeable cations can be replaced by ammonium ions. The zeolite which has been converted into the $NH_4^+$-form is thoroughly washed with deionized water. The resulting mixture is subjected to solid-liquid separation. The solid phase is dried and then heated to 400°–600° C., whereby the zeolite is converted into $H^+$-form for use in the present disproportionating reaction. Where the zeolite to be used is mordenite, clinoptilolite or ZSM-5 zeolite, alkali metal or alkaline earth metal ions can be directly exchanged with hydrogen ions by an aqueous solution of an acid such as hydrochloric acid, nitric acid or sulfuric acid. Here, the concentration of the acidic aqueous solution is generally 6N or lower, especially in a range of 0.5—3N. The amount of the acid to be used is often 2–10 times the amount of cations which are contained in the zeolite and are to be exchanged. In the case of the ion exchange by the acid, 90% or more of ion-exchangeable cations can also be exchanged with hydrogen ions by repeating the ion-exchanging procedures once or more. The zeolite converted into the $H^+$-form by the acidic aqueous solution is similarly washed with deionized water. The resulting mixture is subjected to solid-liquid separation. The solid phase so obtained is dried and then calcined at 400°–700° C. into a catalyst.

The term "ion-exchangeable cations in a zeolite" indicate alkali metal cations and/or alkaline earth metal cations contained in the zeolite. How much of these cations have been exchanged with hydrogen ions by the above exchanging operation can be determined by performing a calculation on the basis of chemical analysis date of the zeolite so obtained.

If the zeolite subjected to the ion-exchanging treatment is in a briquette form or has been formed into tablets, it is used, as is, as a catalyst. If it is in a powdery form, it is extruded into pellets or compressed into tablets in a manner known per se in the art for use as a catalyst. In some instances, it can be granulated into microspheres by a spray drier for use as a fluidized bed catalyst. The particle sizes of these microspheres may preferably be distributed over a range of 20–100 μm.

The disproportionating reaction of trimethylamine in the present invention can be practiced by bringing the trimethylamine along with ammonia into contact with the above-described catalyst layer or a mixture of the trimethylamine, ammonia and methylamines composed primarily of monomethylamine into contact with the 10 above-described catalyst layer. Whichever reaction method is followed, the starting materials which are to be fed to the catalyst layer upon practicing the disproportionating reaction may contain dimethylamine, methanol, dimethyl ether and/or the like in small amounts. In the present disproportionating reaction, the composition of disproportionated products is determined by the ratio of nitrogen atoms to carbon atoms contained in the starting materials of the reaction, the N/C ratio, irrespective of the composition of the starting materials of the reaction. In the method of the present invention, an N/C ratio in a range of 1–50, especially 3–30 is often used.

The temperature of the catalyst layer upon conducting the reaction may preferably be in a range of 270°–400° C. Usually, a temperature in a range of 280°–80° C. is often employed. The preferred reaction pressure may be from atmospheric pressure to 50 atm. A reaction pressure in a range of 10–30 atm is often used. The feed rate of the starting materials of the reaction to the catalyst layer can be in a range of 500–20,000 $Nm^3/m^3hr$ when expressed in terms of gas hourly space velocity (hereinafter abbreviated as "GHSV". GHSV in a range of 1,000–10,000 $Nm^3/m^3hr$ is often employed.

A reactor for use in the present invention can be of the usual fixed bed or fluidized bed type. In the case of the fixed bed type, a shell-and-tube reactor or an adiabatic reactor can be used.

A description will next be made of advantageous effects of the present invention.

The method according to the present invention can bring about such an industrial merit that the disproportionating reaction of trimethylamine can proceed at a temperature lower than those required when conventionally-known amorphous silica-alumina catalysts are used and the supply of reaction heat can hence be facilitated. Further, the method of the present invention can practically achieve complete prevention of by-production of trace impurities such as acetonitrile, thereby making it possible to avoid a reduction in separation efficiency The method of the present invention can effectively be used in combination with a step for producing, from ammonia and methanol, methylamines composed mainly of dimethylamine, monomethylamine as a by-product and not more than 5 percent of trimethylamine as a further by-product, i.e., in combination with a step for producing methylamines, in which a zeolite modified with a silicon compound and having a high shape-selectivity is used as a catalyst.

The present invention will hereinafter be described specifically by examples and comparative examples.

EXAMPLE 1

In 2,500 ml of a 1N aqueous solution of ammonium chloride, 300 g of powdery synthetic mordenite (silica/alumina ratio: 10) were added, followed by external heating for 4 hours under reflux. The resultant mixture was then separated into a solid phase and a liquid phase. To the solid phase so obtained, a fresh supply (3,000 ml) of a 1N aqueous solution of ammonium chloride was added, followed by reflux for 4 hours, whereby $NH_4^+$-form mordenite was obtained. Subsequent to separation of the mixture into a solid phase and a liquid phase, the solid phase was thoroughly washed with deionized water, dried at 120° C. and then calcined at 600° C. for 3 hours under air circulation, whereby $H^+$-form mordenite was prepared. From data of a chemical analysis of the mordenite so obtained, it was found that 97.5% of ion-exchangeable cations in the mordenite had been exchanged with hydrogen ions. The resultant mordenite was compressed into cylindrical tablets of 3 mm in diameter and 3 mm in height and were provided for use as a catalyst.

A stainless-steel reactor having an internal diameter of 25 mm was packed with 20 ml of the catalyst so obtained, followed by external heating over a fluidized sand bath.

A liquefied gas mixture of ammonia and trimethylamine (N/C ratio: 10.1) was fed to the catalyst layer at GHSV of 4,000/hr, followed by a reaction at 330° C. and 20 atm. As a result of an analysis of components at an outlet of the reactor 150 hours after the reaction was started, it was found that the conversion of trimethylamine was 60.8% and no trace by-products such as acetonitrile were detected practically (20 ppm or less). The conversion of trimethylamine reached 60.9% when the analysis was conducted after the reaction was continued for 800 hours and further, no deterioration of the catalyst was recognized.

This example clearly indicates that $H^+$-form mordenite shows high activities at lower temperatures than $SiO_2$—$Al_2O_3$ catalysts widely used to date for the disproportionating reaction and hence, prolongation of the contact time is not needed. This example also teaches that mordenite having a large R ratio features less deposit of carbonaceous substances and no deterioration of the catalytic activities will be observed even in a long-term operation.

EXAMPLE 2

In 2,000 ml of a 2N aqueous solution of hydrochloric acid, 300 g of natural mordenite (mordenite content: 74%) having a granule size range of 2–3 mm were added, followed by gentle stirring at room temperature for 5 hours. After the resultant mixture was separated into a solid phase and a liquid phase, the solid phase was added with a fresh supply (2,000 ml) of a 2N aqueous solution of hydrochloric acid and then treated as above. The resultant mixture was subjected to solid-liquid separation. The solid phase was washed with deionized water, dried, and then calcined at 550° C. for 4 hours, whereby a catalyst was prepared. It was found that 98.2% of ion-exchangeable cations in the mordenite had been exchanged with hydrogen ions. A stainless-steel reactor having an internal diameter of 25 mm was packed with 20 ml of the mordenite so obtained, followed by external heating over a fluidized sand bath.

A liquefied gas mixture of ammonia and trimethylamine (N/C ratio: 10.1) was fed to the catalyst layer at GHSV of 3,200/hr, followed by a reaction at 330° C. and 20 atm. As a result of an analysis of components at an outlet of the reactor 150 hours after the reaction was started, it was found that the conversion of trimethylamine was 61.1% and no trace by-products such as acetonitrile were detected practically (20 ppm or less).

Comparative Example 1

A reactor similar to that employed in Example 1 was packed with 20 ml of an amorphous silica-alumina catalyst (alumina content: 13%) having a granule size range of 2–3 mm. A liquefied gas mixture of ammonia and trimethylamine (N/C ratio: 10.3) was fed to the catalyst layer at GHSV of 4000/hr, followed by a reaction at 330° C. and 20 atm.

As a result of an analysis of components at an outlet of the reactor 150 hours after the reaction was started, it was found that the conversion of trimethylamine was 18.5%.

Comparative Example 2

From mordenite similar to that employed in Example 1, a catalyst whose ion-exchange rate to hydrogen ions was 70% was prepared. Using the catalyst so obtained and the same reactor as that employed in Example 1, a liquefied gas mixture of ammonia and trimethylamine (N/C ratio: 5) was fed to the catalyst layer at GHSV of 1,500/hr, followed by a reaction at 350° C. and 20 atm. The results of an analysis of components at the outlet of the reactor 150 hours after the reaction was started were as follows:

The conversion of trimethylamine was 57.2%, and the total amount of by-products, that is, acetonitrile, acetone, propionitrile and propylamine, was 1,200 ppm.

EXAMPLE 3

From mordenite similar to that employed in Example 1, a catalyst whose ion-exchange rate to hydrogen ions was 83% was prepared. Using the catalyst so obtained and the same reactor as that employed in Example 1, a liquefied gas mixture of ammonia and trimethylamine (N/C ratio: 5) was fed to the catalyst layer at GHSV of 1,500/hr, followed by a reaction at 350° C. and 20 atm. The results of an analysis of components at the outlet of the reactor 150 hours after the reaction was started were as follows:

The conversion of trimethylamine was 60.4%, and the total amount of by-products, that is, acetonitrile, acetone, propionitrile and propylamine, was 380 ppm. Example 4.

In 2,000 ml of a 2N aqueous solution of hydrochloric acid, 300 g of natural clinoptilolite (clinoptilolite content: 75%) having a particle size range of 2–3 mm were added, followed by gentle shaking at room temperature for 4 hours. After the resultant mixture was separated into a solid phase and a liquid phase, the solid phase was separated, followed by the addition of a fresh supply (2,000 ml) of a 2N aqueous solution of hydrochloric acid, The solid phase was treated for four hours at room temperature. The resultant mixture was then subjected to solid-liquid separation. The solid phase so obtained was washed with deionized water, dried, and then calcined at 500° C. for 4 hours, whereby a catalyst was prepared. The ion-exchange rate to hydrogen ions of the catalyst so obtained was 95%.

A reactor similar to that employed in Example 1 was packed with 20 ml of the catalyst so obtained to conduct disproportionation of trimethylamine. One hundred hours after the reaction was started under conditions similar to those employed in Example 1, an outlet gas at the outlet of the reactor was analyzed. As a result, it was found that the conversion of trimethylamine was 56.1% and no trace byproducts such as acetonitrile was detected practically (20 ppm or less).

EXAMPLE 5–12

In each example, a glass-made reactor having an internal diameter of 18 mm was packed with a zeolite catalyst having a granule size range of 1–2 mm. To the catalyst layer, a liquefied gas mixture (N/C ratio: 10) of ammonia and trimethylamine was fed at GHSV of 1,000/hr, followed by a reaction at atmospheric pressure. Results obtained using various zeolites are presented in Table 1. The reaction temperature was 350° C. and in each of the catalysts, the fractional attainment of exchangeable cations to a H-type zeolite was 90% or higher.

TABLE 1

| Example No. | Kind of zeolite | Conversion of TMA* (%) | By-product (ppm) |
|---|---|---|---|
| 5 | Heulandite | 53.8 | 30 |
| 6 | Canncrinite | 46.1 | 25 |
| 7 | Ferrierite | 51.0 | 20 |
| 8 | Gmerlinite | 40.3 | 30 |
| 9 | ZMS-5 (Si/Al = 25) | 58.5 | 37 |
| 10 | Stilbite | 46.9 | 35 |
| 11 | Mazzite | 49.0 | 20 |
| 12 | Offretite | 51.8 | 20 |

*TMA: Trimethylamine

Comparative Example 3

In a reactor and under conditions similar to those employed in Example 1, a disproportionating reaction of trimethylamine was conducted using REY zeolite as a catalyst.

The results of an analysis of components at an outlet of the reactor 150 hours after the beginning of the reaction were as follows:

The conversion of trimethylamine was 67.3%, and the total amount of by-products, that is, acetonitrile, acetone, propionitrile and propylamine was 1,800 ppm.

Comparative Example 4

In a reactor and under the same conditions similar to those employed in Example 1, a disproportionating reaction of trimethylamine was conducted using H-Y zeolite (fractional attainment of exchangeable cations to a H-type zeolite: 90%) as a catalyst.

As a result of an analysis of components at an outlet of the reactor 150 hours after the beginning of the reaction, it was found that the conversion of trimethylamine was 64.1% and substantially no by-products such as acrylonitrile were observed practically (<20 ppm).

The reaction was continued further. An analysis of components at the outlet of the reactor 800 hours after the beginning of the reaction indicated that the conversion of triethylamine dropped to 57.8%.

It has hence been found that in the case of a zeolite having a low R ratio, a decrease in catalytic activities is inevitable in a long-term operation.

I claim:

1. In a method for disproportionating trimethylamine by subjecting the trimethylamine and ammonia or the trimethylamine, ammonia and a methylamine to a disproportionating reaction to reduce the proportion of the trimethylamine, the improvement wherein the disproportionating reaction is conducted in the presence of at least one zeolite selected from the group consisting of mordenite, clinoptilolite, heulandite, canncrinite, ferrierite, gmelinite, stilbite, mazzite, offretite and ZSM-5 zeolite, at least 80% of whose ion-exchangeable cations are in the form of hydrogen ions.

2. A method according to claim 1, wherein at least 90% of the ion-exchangeable cations of each zeolite are in the form of hydrogen ions.

3. A method according to claim 1, wherein each zeolite has a silica/alumina ratio of 10 or greater.

4. A method according to claim 2, wherein each zeolite has a silica/alumina ratio of 10 or higher.

5. A method according to claim 1, wherein said at least one zeolite is selected from the group consisting of mordenite, clinoptilolite and ZSM-5 zeolite.

6. A method according to claim 2, wherein said at least one zeolite is selected from the group consisting of mordenite, clinoptilolite and ZSM-5 zeolite.

7. A method according to claim 1, wherein said at least one zeolite is selected from the group consisting of mordenite and clinoptilolite.

8. A method according to claim 2, wherein said at least one zeolite is selected from the group consisting of mordenite and clinoptilolite.

9. A method according to claim 1, wherein the disproportionating reaction is conducted at from 270° C. to 400° C., from atmospheric pressure to 50 atm and a nitrogen-to-carbon atom ratio, N/C ratio, of from 1 to 50 in the starting materials.

10. A method according to claim 2, wherein the disproportionating reaction is conducted at from 270° C. to 400° C., from atmospheric pressure to 50 atm and a nitrogen-to-carbon atom ratio, N/C ratio, of from 1 to 50 in the starting materials.

11. A method according to claim 3, wherein the disproportionating reaction is conducted at from 270° C. to 400° C., from atmospheric pressure to 50 atm and a nitrogen-to-carbon atom ratio, N/C ratio, of from 1 to 50 in the starting materials.

12. A method according to claim 4, wherein the disproportionating reaction is conducted at from 270° C. to 400° C., from atmospheric pressure to 50 atm and a nitrogen-to-carbon atom ratio, N/C ratio, of from 1 to 50 in the starting materials.

13. A method according to claim 5, wherein the disproportionating reaction is conducted at from 270° C. to 400° C., from atmospheric pressure to 50 atm and a nitrogen-to-carbon atom ratio, N/C ratio, of from 1 to 50 in the starting materials.

14. A method according to claim 6, wherein the disproportionating reaction is conducted at from 270° C. to 400° C., from atmospheric pressure to 50 atm and a nitrogen-to-carbon atom ratio, N/C ratio, of from 1 to 50 in the starting materials.

15. A method according to claim 1, wherein the disproportionating reaction is conducted at from 280° C. to 380° C., from 10 atm to 30 atm and a nitrogen-to-carbon atm ratio, N/C ratio, of from 3 to 30 in the starting materials.

16. A method according to claim 2, wherein the disproportionating reaction is conducted at from 280° C. to 380° C., from 10 atm to 30 atm and a nitrogen-to-carbon atm ratio, N/C ratio, of from 3 to 30 in the starting materials.

17. A method according to claim 3, wherein the disproportionating reaction is conducted at from 280° C. to 380° C., from 10 atm to 30 atm and a nitrogen-to-carbon atm ratio, N/C ratio, of from 3 to 30 in the starting materials.

18. A method according to claim 4, wherein the disproportionating reaction is conducted at from 280° C. to 380° C., from 10 atm to 30 atm and a nitrogen-to-carbon atm ratio, N/C ratio, of from 3 to 30 in the starting materials.

19. A method according to claim 5 wherein the disproportionating reaction is conducted at from 280° C. to 380° C., from 10 atm to 30 atm and a nitrogen-to-carbon atm ratio, N/C ratio, of from 3 to 30 in the starting materials.

20. A method according to claim 6, wherein the disproportionating reaction is conducted at from 280° C. to 380° C., from 10 atm to 30 atm and a nitrogen-to-carbon atm ratio, N/C ratio, of from 3 to 30 in the starting materials.

* * * * *